United States Patent [19]

Bajek

[11] Patent Number: 4,481,833
[45] Date of Patent: Nov. 13, 1984

[54] PARTICLE EXCLUDING SAMPLE PROBE

[75] Inventor: Walter A. Bajek, Lombard, Ill.

[73] Assignee: UOP Inc., Des Plaines, Ill.

[21] Appl. No.: 453,038

[22] Filed: Dec. 27, 1982

[51] Int. Cl.³ .............................................. G01N 1/20
[52] U.S. Cl. ........................... 73/863.21; 73/863.23;
73/863.81; 73/863.41; 137/544; 137/545;
137/550
[58] Field of Search ........... 73/863.21, 863.23, 863.81,
73/863.41, 863.24, 863.25; 137/545, 550, 544

[56] References Cited

U.S. PATENT DOCUMENTS

| 2,356,845 | 8/1945 | Hines | 73/863.81 X |
|---|---|---|---|
| 2,742,788 | 4/1956 | Henton | 73/863.23 X |
| 3,559,491 | 2/1971 | Thoen | 73/863.21 X |
| 3,595,087 | 7/1971 | Starks | 73/422 R |
| 3,803,921 | 4/1974 | Dieterich | 73/422 R |
| 3,921,458 | 11/1975 | Logan | 73/422 R |
| 4,215,565 | 8/1980 | Zanker | 73/863.41 X |

FOREIGN PATENT DOCUMENTS

| 86579 | 12/1921 | Fed. Rep. of Germany | 73/863.23 |
| 1471256 | 3/1967 | France | 73/863.21 |
| 2302521 | 9/1976 | France | 73/863.23 |
| 2490345 | 3/1982 | France | 73/863.21 |
| 1198888 | 7/1970 | United Kingdom | 73/863.23 |
| 626385 | 9/1978 | U.S.S.R. | 73/863.81 |
| 691723 | 10/1979 | U.S.S.R. | 73/863.21 |

OTHER PUBLICATIONS

Unit Operations of Chemical Engineering, 2nd Ed., McCabe and Smith, McGraw-Hill, Inc., pp. 65, 153 and 154.
Transfer Operations, Greenkorn & Kessler, McGraw-Hill, 1972, p. 210.

Primary Examiner—Gerald Goldberg
Assistant Examiner—Tom Noland
Attorney, Agent, or Firm—James R. Hoatson, Jr.; William H. Page, II; Richard J. Cordovano

[57] ABSTRACT

A sampling probe by means of which a sample of fluid free of particles or substantially reduced in particle content can be removed from a particulate matter-containing fluid stream which is flowing in a conduit. This is accomplished by means of probe geometry. Openings for entry of the sample into the probe face downstream. In one embodiment, the cross-section of a probe at the fluid entry area is V-shaped.

12 Claims, 4 Drawing Figures

PARTICLE EXCLUDING SAMPLE PROBE

BACKGROUND OF THE INVENTION

This invention relates to apparatus used in separating a portion of fluid for use as a sample from a flowing stream of fluid. Examples of such apparatus may be found in U.S. Pat. Nos. 3,921,458 (Logan), 3,595,087 (Starks), and 3,803,921 (Dieterich). It can be readily seen that particulate matter in the sampled stream is not excluded from entering the sample probes of these patents. This invention further relates to obtaining a fluid sample which is substantially reduced in particulate content.

The presence of particulate matter entrained in a flowing fluid adds to the difficulty of obtaining a sample of the fluid. Often, particulate matter should not be present in a sample. For example, when a sample stream is allowed to flow to a chromatographic analyzer, particles must be removed from the stream to prevent malfunction of the analyzer. Particle removal from a sample stream can be accomplished by means of apparatus familiar to those skilled in the art such as filters or cyclones. However, such particle removal apparatus must be designed, purchased, installed, and maintained, sometimes at significant cost. Tubing and equipment used to contain and process a sample can become plugged with particles, causing interruption of sample flow. The removed particles must be disposed of in some manner. Thus, it is often desirable to exclude particulate matter at the point of taking a sample, that is, to obtain a sample of fluid only, leaving all particles in the sampled stream. In some cases, a sample may be removed from a flowing stream through filter material immersed in the stream, so that particles collected on the filter material are swept away by the fluid stream. But this may not be feasible due to unavailability of filter material compatible with the stream to be sampled, rapid blinding of the filter material by particulate matter, or other problems.

Though it may not be possible to exclude all particulate matter at the point of sampling, it is desirable to exclude as much as possible, thus reducing the magnitude of the problems associated with the presence of particulate matter. For example, consider a case where a sample system filter rapidly blinds, or clogs, and hinders fluid flow through it, so that it is necessary to change or clean the filter daily. By excluding particles at the point of sampling, the amount of particulate matter collected by the filter might be reduced to a more tolerable level. Changing a disposable filter element or cleaning a reusable element once a week might be acceptable, where changing or cleaning once a day would not.

STATEMENT OF ART

Sample probes of various configurations, such as in the three U.S. patents cited above, are used for taking samples of fluid streams flowing in conduits. Exclusion of particulate matter from sample probes is accomplished by use of barriers to particulates, that is, a filter or screen through which at least a portion of the particles present cannot pass. In most sampling systems, a filter is provided at some point in the sample handling system downstream of the sample probe. In contrast, this invention focuses on the sample probe, which is the start of the sample handling system.

This invention makes use of certain principles of fluid mechanics. Three diagrams and a photograph, all published in texts dealing with fluid mechanics are cited herein. While these diagrams and the photograph are not believed to be pertinent as prior art to the invention, they constitute a part of the art area of the invention and are helpful in understanding the invention.

BRIEF SUMMARY OF THE INVENTION

It is an object of this invention to provide a sample probe by means of which a sample of fluid free of particles or substantially reduced in particle content can be removed from a particulate matter-containing fluid stream which is flowing in a conduit. It is a further object to provide such a probe which requires only a minimal amount of maintenance or no maintenance and which can be installed at a cost little more than that for a probe which does not embody the present invention. In one of its broad embodiments, the present invention comprises a sampling probe which has a hollow interior communicating with a fluid stream by means of fluid entry openings in the probe facing substantially downstream, wherein the hollow interior also communicates with sample handling apparatus, and wherein the shape and orientation of the probe is such that particulate matter is substantially precluded from entering the fluid entry openings. In another embodiment, the invention comprises such a probe wherein at least a portion of the exterior surface of the probe which faces substantially upstream is comprised of two non-parallel planes such that a line formed by the joining of the two planes is parallel to the longitudinal axis of the probe and such that the line is located at that portion of the probe which extends furthest upstream.

Another embodiment can be described as a tubular probe extending into the conduit, the probe having a straight portion located in the conduit at the desired sampling point, with a fluid entry opening being located on the downstream side of said straight portion and facing the direction of fluid flow in the conduit, and means located on said straight portion of the sample probe to create a region of low particulate matter concentration at the fluid entry opening comprising at least two planar flow directing elements extending downstream past the fluid entry opening. The flow directing elements may be formed by machining of the probe or by flat plates attached to the outer surface of the probe.

Other objects and embodiments will become apparent on consideration of this entire specification.

As used herein, the terms "substantially reduced", "substantially precluded", and the like, are used to indicate that a significant amount of particulate is excluded so that a benefit is provided in design, purchase, installation, operation, or maintenance of a sample system. The terms "downstream" and "upstream" are used in the conventional manner. For example, the term "facing downstream" means facing in the direction of flow.

DETAILED DESCRIPTION OF THE INVENTION

Figure 1:
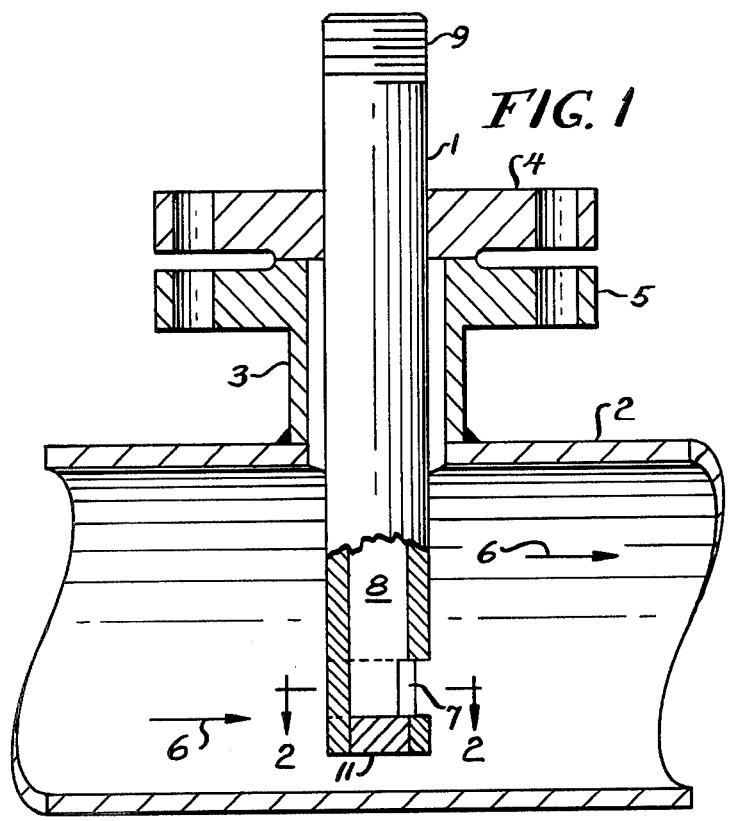
FIG. 1 shows a sampling probe in a cutaway section of pipe, with a portion of the probe also shown as a cutaway section.

For the purposes of promoting an understanding of the principles of the invention, reference will now be made to the embodiment illustrated in the Drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
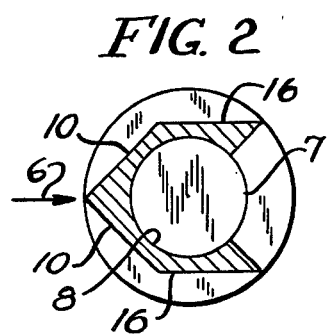
FIG. 2 shows a cross-section of the probe of FIG. 1, taken as indicated by plane 2—2.

FIG. 1 depicts a probe 1 inserted in a pipeline 2 through a flanged nozzle 3. Probe 1 is mounted in a blind flange 4 which has been drilled to accept the outside diameter of probe 1. Weld metal attaching probe 1 to blind flange 4 is not shown. Blind flange 4 is bolted to flange 5, which is part of nozzle 3 (bolts and gasket not shown) in order to position probe 1 in a fluid stream flowing in pipeline 2 in the direction depicted by flow arrows 6. Opening 7 is provided in probe 1 for entry of the sample and is directly opposite the direction of flow of the stream in pipeline 2. This can be clearly seen in FIG. 2. More than one opening may be spaced along probe 1, though further description will be phrased in terms of a single gas entry opening 7. Fluid entering opening 7 flows through the hollow interior 8 of probe 1 to withdrawal conduit (not shown) or other sample handling apparatus (not shown) which is attached to probe 1 by means of threaded portion 9. The end of probe 1 is closed by plug 11, so that the hollow interior 8 communicates with the fluid stream only by means of opening 7. The conduit or other sample handling apparatus could conduct the sample to a chromatographic analyzing system, for example. A valve could be attached to probe 1 to stop the sample flow as necessary.

Referring again to FIG. 2, particles entrained in the fluid stream flowing in pipeline 2 which are sufficiently close to probe 1 to enter opening 7 will strike surfaces 10 and tend to be deflected in a direction which is away from opening 7. Surfaces 10 may be described as planes or planar flow directing elements. A wake comprising large eddies, called vortices, will exist behind probe 1. The amount of particulate matter entrained in the vortices will be reduced as a result of the effect of surfaces 10 in changing the path of particles. The momentum of the particles will cause them to cross flow streamlines which bend around probe 1 toward opening 7 to form eddies and to travel away from the eddies. Also, the geometry of the probe causes the vortices to be displaced a sufficient distance behind the probe and away from opening 7 to reduce the amount of particulate matter in the area of the opening. Thus the fluid in proximity to opening 7 which is drawn into opening 7 to form a sample by means of the difference in pressure between the opening and the sample handling apparatus contains a reduced amount or is substantially free of particulate matter. For more information on the flow of fluids past bodies, consult *Unit Operations of Chemical Engineering* by McCabe and Smith, 2nd edition, McGraw-Hill, 1967, *Transfer Operations* by Greenkorn and Kessler, McGraw-Hill, 1972, and *Fluid Flow* by Sabersky et al., 2nd edition, MacMillan, 1971.

An interesting example pertinent to the principles involved in this invention is provided by the practice of "drafting" in automobile racing. As students of racing well know, if a driver can position his car only a foot or so behind another car, his car will be "sucked along" by a favorable pressure gradient which exists in the wake of the car ahead. This same effect exists in the wake behind a stationary probe in a flowing gas stream. To prevent particles from being drawn into the area of the probe opening, the probe configuration is arranged in accordance with the invention.

A boundary layer forms in the fluid flowing over surfaces of a body immersed in a flowing stream. The boundary layer fluid flows along the surface of the body unless the surface of the body is so configured that a relatively large and abrupt change in its velocity is required for it to continue to adhere to the surface. When a velocity change is too large and abrupt, either in magnitude or direction, the momentum of the fluid prevents it from following and adhering to the surface. Boundary layer separation occurs when the boundary layer fluid no longer adheres but proceeds into the bulk of the fluid. Upon separation, a "backwater" zone of strongly decelerated fluid in which large eddies are formed exists behind the body. This is known as the wake.

Diagrams showing vortices behind a flat plate perpendicular to the flow and a sphere can be seen at pages 65 and 153 of *Unit Operations of Chemical Engineering*. The sphere diagram is also applicable to cylinders, as can be seen in the photograph reproduced on page 210 of *Transfer Operations*. These diagrams aid in appreciating that the distance between the vortices and the body is greater in the case of a flat plate. A diagram of a streamlined body, which can be visualized as an elongated teardrop shape, in a fluid stream can be found on page 154 of *Unit Operations of Chemical Engineering*. The body is configured so that the point of boundary layer separation is moved toward the back of the body and the wake is small. A perfectly streamlined body would have no wake. By considering the flat plate, cylinder, and streamlined body, it can be seen that the configuration of the invention causes the vortices to be displaced a significant distance from the sample inlet opening of the probe.

Returning to FIG. 2, when the particulate matter striking surfaces 10 is hard and likely to abrade or erode the surfaces, they can be specially hardened by use of one of the well known processes appropriate to the material of the surfaces or by means of the deposition of a hard material. Such a material resistant to abrasion and erosion is stellite. In this embodiment of the invention, the exterior surface of the probe is further comprised of two additional planes, designated 16, substantially parallel to one another and the direction of flow, each of which joins a surface 10 to form a line parallel to the longitudinal axis of the probe. These surfaces 16 form an additional barrier to the entry of particles into opening 7. The probe configuration of FIGS. 1 and 2 can be machined from a bar which is originally circular in cross-section.

Figure 3:
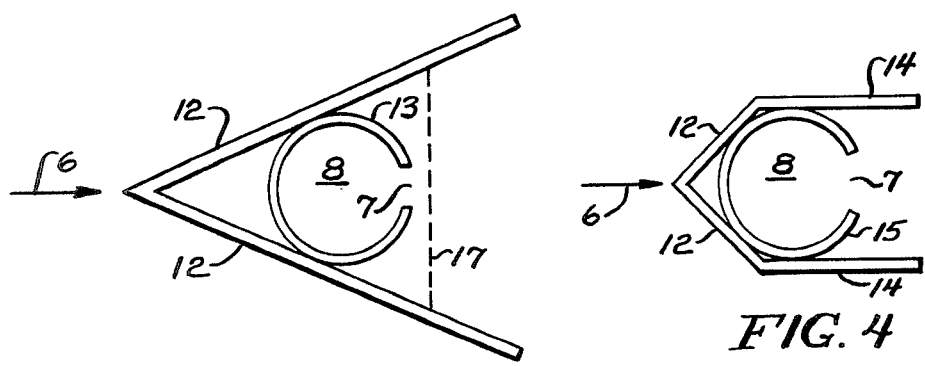
FIGS. 3 and 4 show other embodiments of the invention in the same manner as FIG. 2 but in schematic form with unnecessary detail omitted.
Figure 4:
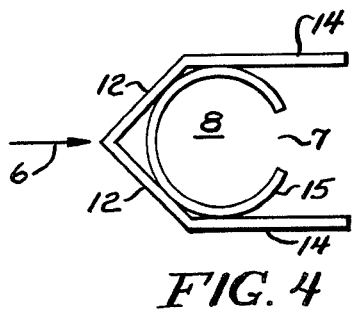

FIGS. 3 and 4 depict different forms of a probe. An opening 7 can be made in a length of pipe 13 or tubing 15 and two pieces of flat stock 12 can be fastened to each other and the pipe or tubing to form the probe (welds or other fastening means not shown). The pieces of flat stock 12 form an exterior surface of the probe which can be described as two non-parallel planes which join upstream of the fluid entry opening. The angle formed by the planes, which faces downstream, is usually in the range of 30° to 110°, but may be greater or smaller. The non-parallel planes shown in FIG. 3 extend downstream of the fluid entry opening in order to assist in excluding particulate. In FIG. 3, a barrier in the form of screen 17 is depicted. The openings of the screen are sized so that at least some particles will not pass through it but so that it will not blind and prevent sample flow. While the screen may be positioned only directly in front of the fluid entry opening, it is better practice in certain applications to extend it so that no fluid can enter the probe without passing through the screen. The screen is an additional feature which may be used in appropriate applications. The screen could be placed directly on pipe 13.

Alternates to screening material for use as a particle barrier include sintered metal filter media, cloth filter media, and perforated plate, all used in a similar manner as the screen. Both a screen and filter material may be used co-extensively. A particle barrier which is perpendicular to the flowing liquid may be placed downstream and in front of gas entry opening 7. It can be held in place by members attaching it to the probe or to the conduit. Typical distances between the fluid entry opening and the barrier, measured along a line parallel to the axis of the conduit, are in the range of 0 to 4 inches. The area of the barrier is preferably several times that of the fluid entry opening. The particle barrier aids in particle exclusion by means of dampening fluid motion in addition to physically excluding particles.

Another method of fabricating a probe embodying the invention is to fasten together lengths of tubing and angle iron in the manner of FIG. 3. In FIG. 4, pieces of flat stock 14 are added to form parallel surfaces such as those of FIG. 2. These parallel planes extend downstream of the fluid entry opening.

Another embodiment of the invention is a configuration which is the same as FIG. 3 or 4 but with pipe 13 or tubing 15 not extending into the "V" formed by the pieces of flat stock 12. Instead, the pipe or tubing would communicate with the interior of the "V" but end in a flat plate closing the top of the "V". In another embodiment, opening 7 would not be made in the pipe or tubing of FIG. 3 or 4 and the sample would enter through the end of the pipe or tubing, the plug (such as shown by item 11 in FIG. 1) being omitted. The end of the pipe or tubing may be cut on a bias so that the plane of the end is facing downstream.

I claim as my invention:

1. A sampling probe to remove a sample of fluid from a particulate matter-containing fluid stream flowing in a conduit which comprises a probe situated relatively perpendicular to said conduit and having a longitudinal axis and an elongated body with an exterior portion and a hollow interior communicating with said fluid stream by means of at least one fluid entry opening in said body, said at least one fluid entry opening facing substantially downstream, wherein said exterior portion of said probe situated opposite said at least one fluid entry opening is comprised of two non-parallel planes, such that a line formed by joining said two non-parallel planes is parallel to said longitudinal axis of said probe and such that said line is located at the furthest upstream portion of said probe and where said non-parallel planes extend downstream of said at least one fluid entry opening.

2. The probe of claim 1 further characterized in that the probe further comprises a particle barrier which has openings of such size that the barrier excludes at least a portion of particulate matter which comes into contact with it.

3. The probe of claim 2 further characterized in that the particle barrier is substantially perpendicular to the flowing fluid and is positioned downstream and in front of said at least one fluid entry opening.

4. The probe of claim 1 further characterized in that the probe has a single fluid entry opening.

5. The probe of claim 1 further characterized in that the surface of said non-parallel planes is specially hardened to reduce abrasion from contact with said particulate material.

6. The sampling device of claim 1 further characterized in that said non-parallel planes are comprised of flat plates attached to the outer surface of the probe.

7. A sampling probe to remove a sample of fluid from a particulate matter-containing fluid stream flowing in a conduit which comprises a probe situated relatively perpendicular to said conduit and having a longitudinal axis and an elongated body with an exterior portion and a hollow interior communicating with said fluid stream by means of a least one fluid entry opening in said body, said at least one fluid entry opening facing substantially downstream, wherein said exterior portion of said probe situated opposite said at least one fluid entry opening is comprised of two non-parallel planes, such that a line formed by joining said two non-parallel planes is parallel to said longitudinal axis of said probe and such that said line is located at the furthest upstream portion of said probe and where said non-parallel planes are in communication with two additional planes substantially parallel to one another to form a line wherein said line is parallel to the longitudinal axis of said probe and each parallel plane is situated substantially parallel to the direction of fluid flow and extend downstream of said at least one fluid entry opening.

8. The probe of claim 7 further characterized in that the probe further comprises a particle barrier which has openings of such size that the barrier excludes at least a portion of particulate matter which comes into contact with it.

9. The probe of claim 8 further characterized in that the particle barrier is substantially perpendicular to the flowing fluid and is positioned downstream and in front of said at least one fluid entry opening.

10. The probe of claim 7 further characterized in that the probe has a single fluid entry opening.

11. The probe of claim 7 further characterzed in that the surface of said non-parallel planes is specially hardened to reduce abrasion from contact with said particulate material.

12. The sampling device of claim 7 further characterized in that said non-parallel planes are comprised of flat plates attached to the outer surface of the probe.

* * * * *